(12) United States Patent
de Jong et al.

(10) Patent No.: US 9,006,471 B2
(45) Date of Patent: Apr. 14, 2015

(54) PROCESS FOR THE PRODUCTION OF FURFURAL FROM PENTOSES AND/OR WATER SOLUBLE PENTOSANS

(75) Inventors: Wiebren de Jong, Maassluis (NL); Gianluca Marcotullio, L'Aquila (IT)

(73) Assignee: Technische Universiteit Delft, Delft (NL)

( * ) Notice: Subject to any disclaimer, the term of this patent is extended or adjusted under 35 U.S.C. 154(b) by 70 days.

(21) Appl. No.: 13/327,123

(22) Filed: Dec. 15, 2011

(65) Prior Publication Data

US 2012/0149924 A1 Jun. 14, 2012

Related U.S. Application Data

(63) Continuation-in-part of application No. 12/944,403, filed on Nov. 11, 2010, now abandoned.

(30) Foreign Application Priority Data

Oct. 27, 2010 (NL) .................................... 2005588
Oct. 26, 2011 (WO) ................ PCT/NL2011/050730

(51) Int. Cl.
*C07D 307/50* (2006.01)

(52) U.S. Cl.
CPC .................................. *C07D 307/50* (2013.01)

(58) Field of Classification Search
CPC ...................................................... C07D 307/50
USPC ............................................................ 549/489
See application file for complete search history.

(56) References Cited

FOREIGN PATENT DOCUMENTS

| DE | 740 602 C | 11/1943 |
|---|---|---|
| DE | 740602 | * 11/1943 |
| WO | 81/00407 A1 | 2/1981 |

OTHER PUBLICATIONS

Hughes et al, Journal of the National Bureau of Standards, vol. 23, p. 293-298 (1939).*
Fonyo, et al: "Comparison of various heat pumpassisted distillation configurations", Chemical Engineering Research and Design, Part A, Institution of Chemical Engineers, deel 76, nr. 3, Mar. 1, 1998, bladzijden 348-360.
C. Moreau et al: "Selective preparation of furfural from xylose over microporous solid acid catalysts", Industrial Crops and Products, deel 7, nr. 2,3, 1998, bladzijden 95-99.
Database Caplus [Online], Chemical Abstracts Service, Columbus, Ohio, US; gevonden in STN accession No. 1988:58188, * samenvatting, RN 12125-02-9 * & E.F. Morosov et al: Gidroliznaya I Lesokhimicheskaya Promyshlenost, nr. 8, 2011, bladzijden 1-2.
Dutch Novelty Search Report issued in Dutch Patent Application No. NL2005588 filed Oct. 27, 2010.

* cited by examiner

*Primary Examiner* — Golam M M Shameem
(74) *Attorney, Agent, or Firm* — Lucas & Mercanti, LLP

(57) ABSTRACT

The invention is directed to a process for production of furfural from pentoses and/or water-soluble pentosans, said process comprising converting said pentoses and/or water soluble pentosans in aqueous solution in a first step to furfural and in a second step feeding the aqueous solution containing furfural obtained in step one to the top of a distillation column to produce an aqueous, liquid downflow, which column is heated at the bottom part thereof, using at least one reboiler to produce an upflow steam flow, recovering a water and furfural containing vapor product stream from the top of said column, compressing said vapor flow and condensing it on the hot side of the reboiler at the bottom of said column to produce sufficient steam in said bottom part of the column to produce said upflow steam flow, and to recover an aqueous furfural containing solution as the condensate in the reboiler.

20 Claims, 1 Drawing Sheet

SCHEME I
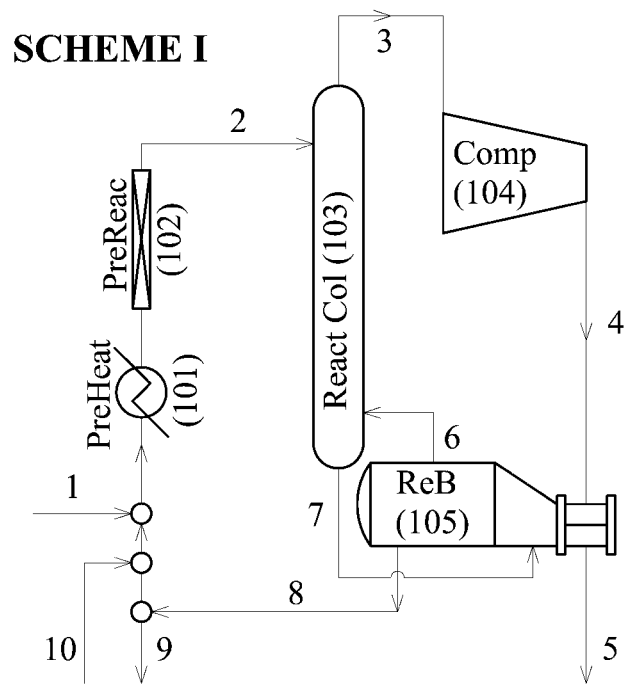
SCHEME II
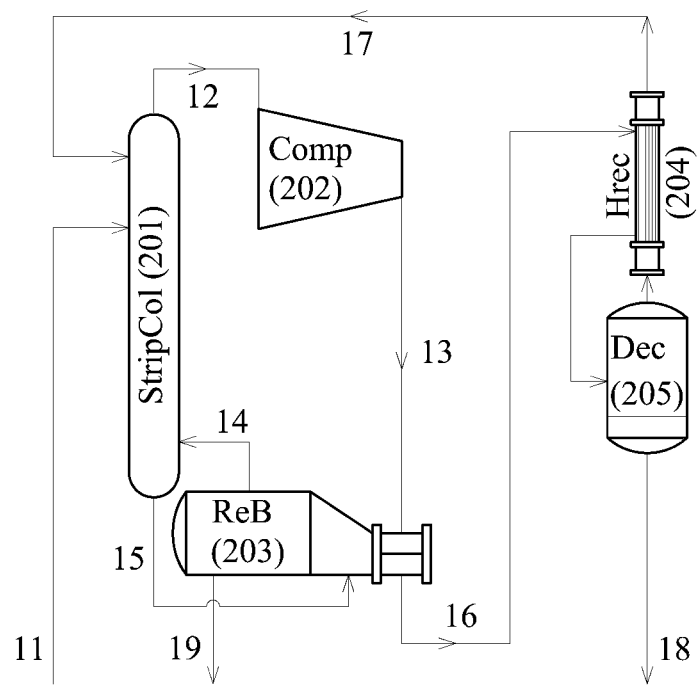
Process sketch

PROCESS FOR THE PRODUCTION OF FURFURAL FROM PENTOSES AND/OR WATER SOLUBLE PENTOSANS

CROSS REFERENCE TO RELATED APPLICATIONS

This patent application is a continuation in part of U.S. Ser. No. 12/944,403 filed Nov. 11, 2011, which in turn claims the benefit of priority from Dutch Patent Application Serial No. 20055888 filed Oct. 27, 2010. This application also claims the benefit of priority from PCT Patent Application Serial No. PCT/NL2011/050730 filed Oct. 27, 2011. The contents of each application are incorporated herein by reference.

FIELD OF THE INVENTION

The invention is directed to a process for the production of furfural (or 2-furancarboxaldehyde) from pentoses and/or water soluble pentosans.

BACKGROUND OF THE INVENTION

Furfural is a chemical intermediate readily available from lignocellulosic biomass, and it is industrially produced since 1921 mainly from residues of agriculture. Furfural offers alternative ways for producing numerous materials as well as new generation biofuels. Potential and upcoming markets for furan resins cover a wide spectrum with massive potential utilization, from wood preservatives to construction materials. In the past furfural has been already used as starting material for the production of important chemical intermediates like THF. Favourable balances between oil prices and furfural availability, as well as green oriented policies, are likely to drive a switch back to the furfural based routes.

As far as the energy sector is concerned, direct hydrogenation derivatives of furfural also have a high potential as alternative liquid fuels and fuel extenders. 2-Methyltetrahydrofuran (MTHF) has been proven to show superior characteristics as fuel extender in regular gasoline, as well as in alternative fuels formulations based on ethanol (P-series fuels). 2-Methylfuran and tetrahydrofurfurylalcohol (THFA) could also be potential candidates as biomass derived octane enhancer, and as diesel fuel additive. Furthermore, by controlled reactions involving furfural, such as aldol condensation, alkylation and etherification, larger molecules may be obtained, that can undergo subsequent hydrogenation/hydrogenolysis to molecules with superior fuel characteristics, such as higher alkanes.

Current furfural production processes are energy intensive and costly. Moreover, they exhibit relatively low yields, 50-60% of the theoretical, and they are poorly integrated with processes aimed at valorising the entire biomass feedstock. This makes furfural less suitable for the fuel industry at the moment, and not always cost competitive with oil derivatives in the chemical industry. The development of novel production processes is needed in order to unlock the potential of this biomass derived platform chemical.

In WO 81/00407 (U.S. Pat. No. 4,366,322) a process for the production of furfural is described, wherein pentoses are converted into furfural at atmospheric pressure and a temperature below 110° C., in a strong acid medium (6N acid). This process shows a low yield and produces a large amount of byproducts. It also has a large energy requirement.

In DE 740602 the production of furfural has been described, using a recycle of part of the product stream to the bottom of the column. This process shows low yield and substantial by-product formation.

Traditional processes employ a large share of their primary energy input to produce high pressure steam to strip out furfural from the reacting system, and for its subsequent purification by distillation. The total energy consumption in such processes ranges from 15 to 50 ton of steam per ton of furfural produced. Nevertheless, the direct reduction of steam usage is usually detrimental for the furfural yield from biomass, and for this reason, despite the related energy costs, plentiful steam stripping is crucial in furfural production.

SUMMARY OF THE INVENTION

Accordingly, it is an object of the present invention to provide a process for the production of furfural from pentoses requiring far less energy, yet allowing for abundant steam stripping.

The present invention is based on the development of a far more energy efficient way of producing furfural from pentoses, or soluble pentosans.

The invention is directed to a process for the production of furfural from pentoses and/or water soluble pentosans, said process comprising converting the said pentoses and/or water soluble pentosans in aqueous solution in a first step to furfural and in a second step feeding the aqueous solution containing furfural obtained in the first step to the top of a distillation column to produce an aqueous, liquid downflow, which column is heated at the bottom part thereof, using at least one reboiler to produce an upflow steam flow, recovering a water and furfural containing vapour product stream from the top of the said column, compressing the said vapour flow and condensing it on the hot side of the reboiler at the bottom of the said column to produce sufficient steam in the said bottom part of the column to produce the said upflow steam flow, and to recover an aqueous furfural containing solution as the condensate in the reboiler.

BRIEF DESCRIPTION OF THE DRAWINGS

FIG. 1 is a schematic flow chart/diagram in accordance with the processes of the invention.

DETAILED DESCRIPTION OF THE INVENTION

There are various ways of carrying out the process of the invention. In a first embodiment, the two steps are carried out simultaneously, i.e. feeding an aqueous solution of one or more pentoses or water soluble pentosans to the top of a reactive distillation column to produce an aqueous, liquid downflow where the reaction partly or totally takes place, which column is heated at the bottom to produce an upflow gaseous water vapour flow, recovering a water and furfural containing product stream from the top of the said column. The resulting product stream can be subjected to a subsequent distillation using conventional methods, or, preferably, a method using the same principles of vapour recompression and heat recovery. Other separation technologies may also be used, such as membranes, adsorption, or similar.

In another embodiment, the two steps are carried out consecutively, namely a first pre-reaction step, wherein an aqueous furfural containing feed stream is produced, for example by heating an aqueous solution of pentoses and/or water soluble pentosans, following which the resulting feed stream is distilled as defined in the present invention. Intermediate solutions are also possible where the reaction is partly carried out before and partly inside the distillation column.

The present invention is based thereon that by using conventional heat recovery systems, the major part of the energy consumption in the process resides in the recompression of the top product of the column. Because of the system vapour-liquid equilibrium, the top and bottom temperatures of the column differ by only few Kelvin. For this reason the energy consumption due to the vapour recompression can be minimal, and such to ensure an appropriate temperature difference between the hot and cold sides of the heat exchanger. By virtue of such energy conservation measure, the external steam (energy) input is minimal, yet plentiful steam stripping may still be applied to the benefit of the overall furfural yields. More in particular it is possible that the steam production in the bottom of the column is fully provided for by the heat available in the said water and furfural containing vapour product stream.

The present invention accordingly resides therein that with the use of an, as such conventional, distillation column, the thermodynamic properties of the system allow for a very efficient and economic production and separation process of furfural from pentoses.

Pentoses and/or soluble pentosans used for this process are preferably obtained from biomass or the residues of biomass conversion. Soluble oligomers of pentoses (pentosans) are sometimes present together with pentoses in liquors containing pentoses. The pentosans are generally depolymerised rapidly under the conditions required for the production of furfural from pentoses, in particular from xylose and arabinose.

As indicated above, current processes for the production of furfural from biomass are very energy intensive, with the consequence that furfural produced in that way, cannot compete with oil based products.

The distillation column or columns to be used herein may be of conventional design, taking into account the requirements of the process. This design can easily be done by a person skilled in the art of distillation. Such a column provides for a sufficient gas/liquid contact. This may be done by the use of packing material, trays (with or without downcomers) and the like.

The process can be performed with or without the use of an acidic catalyst. It is preferred that an acidic catalyst system is present. This may be a mineral or organic acid dissolved in the aqueous liquid downflow in order to attain a pH lower than 3, preferably lower than 1.5. Suitable acids are sulphuric acid, hydrochloric acid or phosphoric acid. However, it is also possible that the interior of the column contains an acidic material on the surface thereof. This material may then be applied to the trays, walls or packing material. Suitable acidic materials to be used herein are acidic zeolites; microporous and mesoporous niobium silicalites; micro-mesoporous sulfonic acids; layered titanates, niobates and titanoniobates; delaminated aluminosilicates; cesium salts of 12-tungstophosphoric acid and mesoporous silica-supported 12-tungstophosphoric acid; bulk and mesostructurated sulfated zirconia; nafion; and a combination of different acid and basic solid catalysts and the like.

In case of the use of an acidic material dissolved in the aqueous liquid downflow, the acidic components are preferably recycled with the bottom product to the column.

According to a further preferred embodiment, the aqueous phase additionally contains a dissolved salt, namely an alkali, earth alkali or ammonium halides, such as common sea salt, NaCl, KCl, $CaCl_2$, $NH_4Cl$, and the equivalent bromides and iodides.

This embodiment may be combined with the use of dissolved acidic material or solid acidic materials anchored to the column or packing material.

Thus, the recycle stream optionally contains the catalyst and it might contain some electrolyte (salt) in order to optimize the catalytic conversion of pentoses into furfural besides enhancing the separation of furfural.

During the gas liquid contact, the pentoses are converted to furfural which at least partly transfers to the gas phase. The gas phase obtained at the top of the column is recompressed and condensed, by heat exchange with the product in the bottom of the column, for example in the reboiler system of the column. The furfural containing condensate can then be used as such in further processes, as concentrated furfural solution, or the furfural may be recovered from it, preferably by further distillation using a column equipped with recompression and condensation of the vapour product. This column may be of comparable construction as the column used for the initial production of furfural.

As indicated above, the pentoses containing feed stream is preferably biomass or biomass derived, for example as secondary product from the paper industry, cellulosic ethanol refineries, sugar factories or anywhere it may become available in suitable amounts. It may also be produced in dedicated facilities where the pentosans are separated from raw biomass material, such as woody biomass, agricultural residues or similar, using different existing technologies, such as steam explosion, dilute acid, alkaline, or hot water hydrolysis, organosolv, supercritical water hydrolysis, different pulping technologies and the like, or a combination these.

The temperature and pressure conditions of the process may vary between relatively wide limits, and depending on the optimization of economic factors. It is preferred to carry out the reaction at temperatures between 100 and 300° C., preferably between 150 and 250° C. The reaction pressure depends on the temperature of choice for the reaction, and will be very similar that of pure saturated water at the same temperature.

The concentration of pentoses in the feed stream is not critical, but it should be such to result in a pentoses concentration inside the reactor(s) preferably below 10 wt. % in water solution, more in particular between 1 and 4 wt. %. The concentration can easily be maintained at this level by the selection of the amount of recycle or simply by dilution.

The invention is now elucidated on the basis of the flow chart in FIG. 1.

In FIG. 1 a process flow diagram has been given. In Scheme I the main reactor column, ReactCol (103), is depicted, together with the main pieces of equipment in a typical configuration for the production of a furfural-water stream (stream 5) from a pentosan sugars containing liquor (stream 1). In Scheme II a distillation system is depicted for the production of concentrated furfural (95 wt %), stream 18, from a more diluted (<8 wt %) furfural containing water stream (stream 11).

On the basis of a process as described in FIG. 1, a feed stream (1) containing an aqueous solution of pentoses and/or soluble pentosans is mixed with a recycle stream, adjusted to the desired temperature in a heater, PreHeat (101) and thus conveyed to the main reactive distillation column, ReactCol (103). To variable extents the reaction can be performed also in a pre-reactor, PreReac (102). The reactive liquid solution (stream 2) enters the reactive column (ReactCol (103)) from a top stage and it is held-up inside the column for a residence time sufficiently long to reach the desired conversion of pentoses. The bottom product of such column (stream 7) enters a boiler, ReB (105) where it is partly vaporized to produce the upflow vapour stream (6). Such stream (6) flowing upward it is enriched in furfural to the expenses of the down-flowing reactive solution, which leaves the column (stream 8) largely deprived of its furfural content. The column gaseous product stream (3) is thus compressed (Comp (104)) and sent (stream 4) to the hot side of the boiler (Reb (105)) where it condenses. The condensed product of Reb (105), stream (5), contains the produced furfural in the form of a dilute aqueous solution. The sump fraction of the reboiler ReB (105), stream (8), can contain the by-products of the reaction, unreacted sugars and smaller amounts of furfural. In case homogeneous catalysis is opted for, stream 8 may contain dissolved acids, metal halides or other soluble material used as catalysts for the reaction. Amounts of such stream (8) can be recycled, or leave the process (stream 9). A stream of pure water or an acid/salt solution of appropriate concentration (stream 10) can be used to replenish the system so to avoid the accumulation of impurities within the process. Stream 10 can preferably be produced from stream 9 after its purification from organic compounds and other impurities thereof.

A dilute aqueous furfural stream of the kind of stream 5, can be concentrated using a traditional furfural-water distillation process, or preferably using a distillation column energized by the recompression and condensation of the vapour products, as depicted in FIG. 1, scheme II. In such scheme a furfural-water stream (11) is fed to a distillation column StripCol (201) to an appropriate stage, and flowing downward is deprived of its furfural content. At its bottom the column is equipped with a reboiler, Reb (203), to produce appropriate amounts of upflow stream (14). The furfural-rich top product of such column (stream 12) is compressed and fed to the hot side of the same reboiler ReB (203) condensing therein to liquid state. The stream 16 so produced is cooled and collected in a decanter, Dec (205), where liquid-liquid separation takes place due to the partial miscibility of furfural with water. According to the common furfural-water separation techniques the heavier phase (stream 18) containing concentrated furfural (95 wt % ca.) is collected whereas the lighter fraction from the decanter (Dec (205)), containing furfural to appreciable extents, is heated up in a recovery heat exchanger, Hrec (204), and fed again to the distillation column StripCol (201).

The invention is now further described on the basis of the following, non-limiting example.

Example

The reaction temperature for this example is 200° C. A liquid aqueous stream of 100 kg/h containing 5 wt. % of dissolved pentoses, derived from the hydrolysis of lignocellulosic biomass, is fed to the process (stream 1), and mixed with a recycle stream of 150 kg/h, at 200° C., containing an amount of unreacted pentoses, small amounts of furfural and some other by-products.

The resulting aqueous mixture stream of 250 kg/h containing 2.03 wt. % of pentoses is adjusted to the reaction temperature (200° C.) in the pre-heater (PreHeat (101)), and fed to an adiabatic pre-reactor (PreReac (102)). Downstream, the pre-reactor (PreReac (102)) stream 2 containing 0.71 wt. % of xylose and 0.87 wt % of furfural is fed to the column (ReacCol (103)) at 200° C.

A liquid bottom product stream (8) of 150 kg/h, containing 0.087 wt. % furfural and 0.05 wt. % pentoses, leaves the column at 200° C. A top vapour product, stream (3), of 100 kg/h leaves the column at 199.8° C. This stream (3), containing 2.70 wt. % of furfural, is compressed (Comp (104)) from 15.6 to 18.7 bar (abs) (pressure ratio 1.2) resulting in stream (4), which is sent to the hot side of the reboiler (ReB 105) where it is condensed.

With the isentropic efficiency of the compressor (Comp (104)) being 0.8, stream 4 temperature results 226° C., whereas its dew point temperature is 209° C. In this way an appropriate temperature difference between the two sides of the reboiler is ensured. Under these conditions, the power required to drive the compressor is 1.3 kW, whereas the heat duty at the reboiler is 53.2 kW, resulting in a coefficient of performance of 40.9. The molar yield of furfural in the stream 5 is 84.5% on the basis of the initial pentoses content of stream 1, and the mechanical energy required to the process is 481 kWh per ton of furfural.

The product stream 5, with a flow of 100 kg/h and containing 2.7 wt % of furfural, is subjected to distillation at atmospheric pressure according to FIG. 1, scheme II. Thus stream 11, which equals stream 5, is fed to the stripping column (StripCol(201)) at an intermediate stage. The top product of the column, stream 12, consists of a vapour aqueous stream of 30 kg/h at 97.9° C. and atmospheric pressure, containing 16.2 wt. % furfural. Such stream 12 is compressed (Comp(202)) to 1.35 bar, resulting in a temperature of 131° C. The dew point temperature of stream 13 is 108° C., so to allow for a sufficient temperature difference at the reboiler (Reb(203)), which operates at the cold side at about 100° C. The top product from the decanter Dec(205) is a stream of 27.2 kg/h containing 8.1 wt. % furfural which is fed to the top of the stripping column after heating (stream 17). The bottom product of the decanter Dec(205), stream 18, represents the main product stream, having a flow of 2.8 kg/h and containing 95.2 wt. % furfural. Nearly 99% of the furfural fed to the system through stream 11 is recovered in stream 18. Under these conditions, the power required to drive the compressor (Comp(202)) is 0.48 kW, whereas the heat duty at the reboiler (Reb(203)) is 16.5 kW, resulting in a coefficient of performance of 34.5. The mechanical energy required to the distillation process is 180 kWh per ton of furfural in stream 18.

The invention claimed is:

1. Process for the production of furfural from pentoses and/or water soluble pentosans, said process comprising converting the said pentoses and/or water soluble pentosans in aqueous solution in a first step to furfural under acidic conditions and in a second step feeding the aqueous solution containing furfural obtained in the first step to the top of a distillation column to produce an aqueous, liquid downflow, in which liquid downflow at least one acidic material is present in an amount of at most 0.5 N and which liquid additionally contains at least one salt selected from the group of alkali, earth alkaline and ammonium halides, which column is heated at the bottom part thereof, using at least one reboiler to produce an upflow steam flow, recovering a water and furfural containing vapour product stream from the top of the said column, compressing the said vapour flow and condensing it on the hot side of the reboiler at the bottom of the said column to produce sufficient steam in the said bottom part of the column to produce the said upflow steam flow, and to recover an aqueous furfural containing solution as the condensate in the reboiler.

2. Process according to claim 1 for the production of furfural from pentoses, which process comprises feeding an aqueous solution of one or more pentoses or soluble pentosans to the top of a distillation column to produce an aqueous, liquid downflow, which column is heated at the bottom part thereof, using at least one reboiler to produce an upflow steam flow, recovering a gaseous water and furfural containing product stream from the top of the said column, compressing the said vapour flow and condensing it on the hot side of the reboiler at the bottom of the said column to produce sufficient steam in the said bottom part of the column to produce the said upflow steam flow.

3. Process according to claim 1, wherein the first step and the second step are carried out consecutively.

4. Process according to claim 1, wherein the acidic material is a mineral acid.

5. Process according to claim 4, wherein the mineral acid is sulphuric acid, phosphoric acid or hydrochloric acid.

6. Process according to claim 1, wherein the distillation column contains a solid acid.

7. Process according to claim 6, wherein the solid acid in the distillation column is on packing material or trays in the distillation column.

8. Process according to claim 3, wherein the reaction is partly carried out before and partly inside the distillation column.

9. Process according to claim 1, wherein the said gaseous product stream is recompressed and led through a heat exchanger which is in contact with the contents of the said column and said heat exchanger is optionally at a location near the bottom thereof.

10. Process according to claim 1, wherein the said aqueous solution of pentoses is obtained from biomass or from a biomass residue.

11. Process according to claim 1, wherein the said product stream is condensed to produce a concentrated aqueous furfural product stream.

12. Process according to claim 8, wherein furfural is recovered from the said concentrated aqueous furfural product stream by distillation with vapour recompression.

13. Process according to claim 1, wherein the pressure in the said distillation column is between 1 and 50 bar(abs).

14. Process according to claim 1, wherein the temperature in the said distillation column is between 100 and 300° C.

15. Process according to claim 14, wherein the temperature in the said distillation column is between 150 and 250° C.

16. Process according to claim 1, wherein the concentration of pentoses during the reactive steps is lower than 10 wt. %.

17. Process according to claim 16, wherein the concentration of pentoses during the reactive steps is between 1 and 4 wt %.

18. Process according to claim 1, wherein the temperature in the said distillation column is between 150 and 250° C.

19. Process according to claim 1, wherein part of the pentoses and/or water soluble pentosans is converted into furfural before said distillation column and partly inside said distillation column.

20. Process according to claim 18, wherein part of the pentoses and/or water soluble pentosans is converted into furfural before said distillation column and partly inside said distillation column.

* * * * *